(12) United States Patent
Herslöf et al.

(10) Patent No.: US 7,202,087 B2
(45) Date of Patent: *Apr. 10, 2007

(54) ANTICOAGULANT COMPOSITION

(75) Inventors: Bengt Herslöf, Stockholm (SE); Per Tingvall, Norberg (SE)

(73) Assignee: LTP Lipid Technologies Provider AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/516,858

(22) PCT Filed: Jun. 12, 2003

(86) PCT No.: PCT/SE03/00973

§ 371 (c)(1),
(2), (4) Date: Jul. 21, 2005

(87) PCT Pub. No.: WO04/000332

PCT Pub. Date: Dec. 31, 2003

(65) Prior Publication Data

US 2006/0165780 A1    Jul. 27, 2006

(30) Foreign Application Priority Data

Jun. 20, 2002   (SE)   .................... 0201922

(51) Int. Cl.
*G01N 31/00* (2006.01)
*G01N 33/92* (2006.01)
*A61K 9/20* (2006.01)
*A61K 31/727* (2006.01)

(52) U.S. Cl. .............. 436/18; 436/8; 436/71; 252/408.1; 424/464; 424/474; 514/56

(58) Field of Classification Search ............ 436/8, 436/18, 71; 252/408.1; 424/450, 464, 474, 424/489, 727; 428/402.2; 514/56
See application file for complete search history.

(56) References Cited

U.S. PATENT DOCUMENTS

| 5,082,667 A | 1/1992 | Van Scoik | |
| 5,626,869 A | 5/1997 | Nyqvist et al. | |
| 5,665,379 A * | 9/1997 | Herslof et al. | 426/450 |
| 5,716,639 A * | 2/1998 | Carlsson et al. | 424/450 |
| 2003/0161884 A1* | 8/2003 | Rosenberg et al. | 424/486 |
| 2005/0020539 A1* | 1/2005 | Ajani et al. | 514/56 |

FOREIGN PATENT DOCUMENTS

| EP | 0368247 A2 | 5/1990 |
| WO | WO-92/05771 A1 | 4/1992 |
| WO | WO-93/19737 A1 | 10/1993 |
| WO | 01/66086 * | 9/2001 |
| WO | WO-01/91729 A1 | 12/2001 |
| WO | WO-02/47663 A1 | 6/2002 |
| WO | WO-03/49721 A1 | 6/2003 |
| WO | 03/068267 * | 8/2003 |

OTHER PUBLICATIONS

European Journal of Pharmaceutical Sciences, vol. 1, 1994, L. Lohikangas et al.; "Relative contribution of phosphatidylcholine and monoglyceride to absorption enhancement of low molecular weight heparin (Fragmin) by a new lipid-based drug delivery system in monolayers of human intestinal epithelial Caco-2 cells and after rectal administration to rabbits"; pp. 307-312, abstract 3.1, 3.3, discussion.

* cited by examiner

*Primary Examiner*—Maureen M. Wallenhorst
(74) *Attorney, Agent, or Firm*—Dickstein, Shapiro, LLP.

(57) ABSTRACT

A solid heparin tablet composition has a melting point of 25° C. or higher and is a continuous lipid component containing one or more polar lipids, one or more non-polar lipids, optionally one or several of water and mono- to trivalent alcohol in an amount of up to 15% by weight of the composition, and native heparin or fractionated heparin. Also described is a corresponding tablet, processes for production of the composition and the tablet, and a method of preventing or treating conditions amenable to preventive or therapeutic treatment by administration of the tablet.

21 Claims, No Drawings

ANTICOAGULANT COMPOSITION

FIELD OF THE INVENTION

The present invention relates to an oral heparin tablet composition, a corresponding tablet, and to corresponding methods of manufacture.

BACKGROUND OF THE INVENTION

Heparin, whether normal (native, not fractionated) or partially degraded (fractionated), is an important anticoagulant. It is administered to persons with increased risk for blood clot formation, such as persons having undergone surgery or severe trauma or whose blood coagulation system is not well balanced, such in persons with risk for deep venous thrombosis. The drawback with this cheap and efficient drug is the requirement of administration by injection.

OBJECTS OF THE INVENTION

It is an object of the invention to provide an oral heparin tablet composition that exploits the advantageous properties of lipids as pharmaceutical carriers in regard of gastroinstestinal uptake and/or sustained release and/or convenience and/or economy.

It is another object of the invention to provide a corresponding carrier composition for incorporation of heparin.

It is a further object of the invention to provide processes for making the aforementioned carrier composition and for incorporating heparin into said carrier composition.

Further objects of the invention will be evident from the following short description of the invention, the description of preferred embodiments, and the appended claims.

SHORT DESCRIPTION OF THE INVENTION

According to the present invention is disclosed a solid heparin composition for oral administration which has a melting point of from 25° C. to 50° C. or more, preferably from 30° C. to 45° C., more preferred from 33° C. to 42° C., comprising a continuous lipid phase comprising, preferably consisting of, a polar lipid component, a non-polar lipid component, and a pharmacologically efficient amount of heparin which may be native (non-degraded) or degraded (fractionated) heparin. The polar lipid component consists of one or more polar lipids. The non-polar component consists of one or more non-polar lipids. The one or more polar lipids are membrane lipids, in particular glycolipids and phospholipids. The one or more non-polar lipids are preferably glycerides, i.e. glycerol esters of fatty acids (mono-, di-, and triglycerides). All polar and non-polar lipids of the invention can be sourced from foodstuffs or food grade material. The polar lipids of the invention are amphiphilic with headgroups such as galactose or phosphate esters. The polar lipid component of the invention is combined with the non-polar lipid component in various proportions to allow the controlled incorporation of pharmaceutical including food supplement agents. It is believed that the incorporation mechanism is based on interactions of the polar headgroups and the lipophilic chains of the non-polar component with the compound to be incorporated. Pharmacologically efficient compositions for heparin, optionally in admixture with other pharmacologically active agents, can be experimentally determined by varying the ratio of the polar to non-polar component. To a certain extent the pharmacological efficacy of the composition is also influenced by the composition of the polar and non-polar component, respectively.

Preferably the polar component of the solid heparin composition according to the invention comprises or, more preferred, consists of one or several polar lipids of vegetable origin, such as oat kernels or soybeans. Preferably the non-polar lipid component of the composition according to the invention comprises or, more preferred, consists of one or several glycerides of vegetable origin, such as palmkernel oil, coconut oil, palm oil and cottonseed oil.

It is particularly preferred for the solid heparin composition of the invention to comprise lipid material of vegetable origin only.

According to the present invention is also disclosed a solid heparin oral tablet produced from the aforementioned pharmaceutical or food supplement composition, in particular by compression moulding or casting.

In the pharmaceutical literature lipid continuous phases are described as oily liquids, which need to be administered as oral liquids or enclosed in hard or soft shell capsules. However, such oily liquids are completely outside of the scope of the present invention. Lipid phases are also known in form of dispersions, i.e. dispersed aqueous solvents. Lipid emulsions and liposome preparations are examples of such dispersions which, by definition, are not lipid continuous phases and therefore do not form part of the present invention.

The polar component of the invention can be described as formed of membrane lipid(s), i.e. the lipid constituents of biological membranes. Membrane lipids contain a polar, hydrophilic, head group and one or more lipophilic hydrocarbon chains. This combination makes the membrane lipid molecules amphipathic and enables them to associate both with water and oils. Such membrane lipids can be classified according to their chemical structure, which is a function of how the polar head group is linked to the lipophilic chains. Sphingolipids (linked by sphingosine) and glycerolipids (linked by glycerol) are the two main groups. Depending on the characteristics of the polar head group sphingolipids and glycerolipids can be further classified as phospholipids, with the head group being a phosphate ester, or as glycolipids, with the head group being a carbohydrate. Depending of the specific nature of the carbohydrate group membrane lipids sometimes are called, for example, galactolipids, which are glycerolipids with galactose in the polar head group. Examples of common membrane lipids are phosphatidylcholine (PC), phosphatidylethanolamine (PE), and digalactosyldiacylglycerol (DGDG). The membrane lipids can be extracted from, for example, egg yolk (egg lecithin), milk and dairy products, soybeans (soy lecithin), other oil crops, oat kernels, and other cereals and grains. These extracts can be further treated to become, for example, PC from soybeans and galactolipids from oats. Preferred polar lipids are galactolipids from oat kernels (CPL-galactolipid) or from soybeans (soy lecithin or soy-PC).

Synthetic polar lipids and membrane lipid analogues based on a carbohydrate or phosphate ester moiety are comprised by the polar lipid component of the invention.

The preferred non-polar lipids of the invention are fatty acid esters of glycerol. These esters include mono-, di-, and triglycerides. Edible oils are triglyceride oils, from which mono- and diglycerides can be derived. Other non-polar lipids of the invention include vegetable and animal oils from various sources, synthetic oils, fatty acids, natural and synthetic glycerides, sterol esters, fatty alcohols. Synthetic non-polar lipids and fatty acid analogues are also comprised by the invention. A description of the area of polar and non-polar lipids is given in "Fatty Acid and Lipid Chemistry" (Frank Gunstone, 1996, Blackie Academic & Professional, Chapman & Hall).

The triglyceride may be selected from palmkernel oil or natural oils with similarly, relatively high solid fat content or melting range. Preferred non-polar lipids include palmkernel oil fractions, obtained by commercial fractionation of palmkernel oil into specific mixtures of triglycerides, e.g. palmkernel stearin, based on the combination of mainly lauric, myristic, and palmitic esters of glycerol. Preferred monoglycerides are selected from edible oil derived monoglycerides, in particular medium chain monoglycerides (chain length $C_8$–$C_{10}$), derived from coconut oil, and normal chain monoglycerides (chain length $C_{16}$–$C_{18}$), derived from most vegetable oils.

According to a preferred aspect of the invention the continuous lipid phase may comprise up to 15% by weight, preferably up to 10% by weight, most preferred up to 5% by weight of water and/or an alcohol, including a alkanediol or -triol, such as ethanol, 1,2-propylene glycol, low molecular weight polyethylene glycol, and glycerol. By definition the continuous lipid phase cannot comprise more water or alcohol than is compatible with its property of being continuous.

According to the invention is also disclosed a carrier composition for heparin consisting of a continuous lipid phase having a melting point of from 25° C. to 50° C. or more, preferably from 30° C. to 45° C., more preferred from 33° C. to 42° C., comprising, preferably essentially consisting of, a polar lipid component in combination with a non-polar lipid component.

According to the present invention is furthermore disclosed a process for the production of a heparin tablet composition which has a melting point of from 25° C. to 50° C. or more, preferably from 30° C. to 45° C., more preferred from 33° C. to 42° C., comprising a continuous lipid phase comprising, preferably consisting of, a polar lipid component, a non-polar lipid component and native (essentially non-degraded) or fractionated (degraded) heparin, comprising mixing a polar lipid component with a non-polar lipid component at a first temperature at which at lease one of said components is in a liquid state, thereby obtaining a liquid continuous lipid phase, dissolving a pharmacologically effective amount of heparin in the liquid continuous lipid phase, cooling the solution thus obtained or aliquots thereof to a second temperature at which it solidifies, said second temperature ranging from 25° C. to 50° C. or more, preferably from 30° C. to 45° C., more preferred from 33° C. to 42° C. The cooling may produce a cake if carried out in bulk or a powder if the liquid product is fed to a nozzle, preferably at a temperature slightly above its melting point, and sprayed on, for instance, a cooled metal surface, in particular a polished chromium plated stainless steel surface in form of a band running on rollers. A powderous product may also be obtained by spraying the liquid product into a atmosphere of a temperature below the solidification temperature of the liquid product. The cake may be transformed into powder by, for instance, grinding at a low temperature.

According to a second preferred aspect is disclosed a heparin tablet of the invention coated with one or several layers of tablet coating excipients, such as to provide the tablet with an enteric coat and/or a coat physically stabilizing the tablet at a temperature at or above its melting point, and a corresponding coating process. Particularly preferred is a tablet of the invention provided with a first or only coat applied by a dry coating process comprising mechanically working a coating powder into the surface of the tablet at a temperature at which the tablet is sufficiently soft for the powder particles to adhere and allow them being worked into its surface but not sufficiently soft for substantial deformation, in particular at a temperature from 25° C. to 10° C. below the melting point of the tablet. One or more additional layers may be added to the thus coated tablet by routine pharmaceutical coating processes known in the art. The tablet of the invention may also be built up around an inert nucleus.

A tablet according to the invention can be produced from the heparin oral tablet composition of the invention by compressing the aforementioned powderous product or by moulding or any other suitable process. According to a preferred aspect of the invention the moulding is carried out in a mould covered with an anti-adhering agent or layered By way of examples it was surprisingly found that the solid heparin oral tablet composition of the invention increases the uptake of heparin in the gastrointestinal tract and/or prolongs its efficacy.

In the following the invention will be explained in more detail by the following, non-limiting examples.

DESCRIPTION OF PREFERRED EMBODIMENTS

Materials. The lipid materials used are listed in Table 1.

TABLE 1

Lipid materials
Trade name and source

Galactolipids from oats (CPL-Galactolipid; Lipid Technologies Provider AB, Karlshamn, Sweden)
Medium chain monoglyceride (Akoline MCM; Karlshamns AB, Karlshamn Sweden)
Palmkernel stearin (fraction of palmkernel oil; Karlshamns AB, Karlshamn Sweden)
Heparin (low molecular weight; Calbiochem, p. no. 375097
Hydrogenated cotton seed oil (Akofine NF; Karlshamns AB, Karlshamn Sweden)

EXAMPLE 1

Preparation of a Tablet by Casting Molten Lipid Mixture into a Mould.

Tablet ingredients (in g) are shown in Table 2.

TABLE 2

| | Tablet composition | | | |
| | Tablet preparation | | | |
| | A | B | C | D |
| Heparin* | 0.08 | 0.18 | 0.21 | 0.0 |
| Water | 0.40 | 0.90 | 0.70 | 0.70 |
| Monoglyceride | 0.92 | 0.90 | 0.72 | 0.70 |
| CPL-Galactolipid | 1.24 | 2.79 | 2.17 | 2.17 |
| Palmkernel stearin | 1.40 | 3.15 | 2.31 | 2.52 |

*Low Molecular Weight Heparin (LMWH)

The ingredients were blended and the mixture melted by heating to a temperature of 60 C and stirred at this temperature for 5 hours when all heparin had dissolved. Aliquots (0.24 g) of the melted phase were cast in a mould covered with hydrogenated triglyceride (Akofine NF™) powder. The mould was cooled in a freezer and the tablets recovered.

EXAMPLE 2

Animal Study.

NZW rabbits were used in all experiments and tablets were administered orally. The animals were given four or six tablets followed by water until they had swallowed the tablets. The animals were deprived of food for about 18 hours before dosing. Blood samples were drawn from the ear veins in sodium citrate vials before dosing and ½, 1, 4, 6, and 8 hours after dosing for determination of APTT (Activated Partial Thromboplastin Time) on an IL Coagulation Systems ACL 2000 apparatus. The blood samples were centrifuged for 10 minutes at approximately 1270 G to obtain plasma for the analysis.

The results expressed as % change from baseline were individually calculated for each animal. The APTT value in the blood sample taken prior to dosing is regarded as baseline for each animal. The results are shown in Table 3.

TABLE 3

APTT measurements in rabbits

| Tablet Preparation (LMWH IU/kg) | Time after dosing (hours) | | | | | | | No. of animals |
|---|---|---|---|---|---|---|---|---|
| | 0 | 0.5 | 1 | 2 | 4 | 6 | 8 | |
| A - 475 | 0 | 47 | 51 | 63 | −5 | 35 | 8 | 3 |
| B - 700 | 0 | −9 | 51 | 23 | 35 | 26 | −14 | 4 |
| C - 1000 | 0 | 30 | 39.5 | 47 | 42.5 | 57 | 52.3 | 3 |
| D - 0 | 0 | −15 | 4 | 6 | −22 | −9 | −5 | 7 |

The invention claimed is:

1. A solid oral heparin composition which has a melting point of 25° C. or higher, consisting essentially of a continuous lipid component which is a combination of (a) at least one polar lipid which is a glycolipid and (b) at least one non-polar lipid which is a glyceride, at least one of water and mono- to trivalent alcohol in an amount of up to 15% by weight of the composition, and heparin selected from the group consisting of native heparin and fractioned heparin.

2. An oral heparin tablet comprising the solid oral heparin composition of claim 1 disposed in the form of a tablet.

3. The oral heparin tablet of claim 2 consisting essentially of the solid oral heparin composition, and optionally comprising an inert nucleus.

4. The oral heparin tablet of claim 2, having at least one pharmaceutical excipient coating thereon and optionally comprising an inert nucleus.

5. A method of treating or preventing a condition amenable to treatment or prevention by administration of a pharmacologically effective dose of heparin, wherein the heparin is administered to a human in form of the tablet of claim 2.

6. The method of claim 5, wherein said condition is a member selected from the group consisting of deep venous thrombosis, blood clots, pulmonary embolism, unstable angina, atrial fibrillation, acute myocardial infarction, coronary angioplasty, stent placement, coronary artery bypass graft, pulmonary embolism, and stroke.

7. The oral heparin tablet of claim 2, wherein the composition consists essentially of at least one polar lipid, at least one non-polar lipid, water up to 15% by weight, and said heparin.

8. The oral heparin tablet of claim 2, wherein said at least one polar lipid is a membrane lipid.

9. The oral heparin tablet of claim 2, wherein said at least one non-polar lipid is a glyceride ester of a fatty acid or is of vegetable origin.

10. The oral heparin tablet of claim 9, wherein said at least one non-polar lipid comprises triglycerides from palmkernel oil fractions obtained by fractionation of palmkernel oil or is a $C_8$–$C_{10}$ monoglyceride or $C_{16}$–$C_{18}$ monoglyceride.

11. The oral heparin tablet of claim 2, wherein the composition contains water and at least one mono- to trivalent alcohol.

12. The oral heparin tablet of claim 11, wherein the alcohol is ethanol and optionally, a divalent to trivalent alcohol selected from the group consisting of 1,2-propylene glycol, low molecular weight polyethylene glycol and glycerol.

13. The oral heparin tablet of claim 12, wherein the amount of water is up to 5% by weight.

14. The solid oral heparin composition of claim 1 in which the melting point is 30° C. or higher.

15. A process for the production of an oral heparin tablet which has a melting point of from 25° C. and higher, comprising:
  mixing at least one polar lipid which is a glycolipid with at least one non-polar lipid which is a glyceride at a first temperature at which at least one of said polar lipid and non-polar lipid components is in a liquid state, forming a liquid continuous lipid phase,
  dissolving, in the liquid continuous lipid phase obtained, heparin selected from the group consisting of native heparin and fractionated heparin, forming a solution of heparin,
  cooling the solution of heparin in the lipid phase or portions thereof to a second temperature at which it solidifies, the second temperature being at least 25° C., wherein the cooling comprises forming tablets with aliquots of the solution or from a bulk obtained by the cooling.

16. The process of claim 15, wherein said solution is cooled in bulk forming a cooled bulk product.

17. A process for the production of an oral heparin tablet in which the cooled bulk product of claim 16 is compressed into a tablet.

18. The process of claim 15, wherein said solution is fed to a nozzle and sprayed on a surface or into a cavity having a temperature below the melting point of the liquid.

19. The process of claim 15, wherein the cooling is carried out by pouring an aliquot of said solution into a mould, thereby forming a tablet.

20. The process of claim 15, comprising coating said tablet with at least one powderous pharmaceutical excipient.

21. The process of claim 20, wherein said excipient is mechanically worked into the surface of the tablet so as to form a coating.

* * * * *